United States Patent
Wahi et al.

(10) Patent No.: US 9,737,497 B2
(45) Date of Patent: Aug. 22, 2017

(54) ELECTROSTATICALLY CHARGED NASAL APPLICATION METHOD AND PRODUCT FOR MICRO-FILTRATION

(71) Applicant: TRUTEK Corp., Somerville, NJ (US)

(72) Inventors: Ashok Wahi, Basking Ridge, NJ (US); John Lawrence Dequina, Bridgewater, NJ (US); Kanika Wahi, Basking Ridge, NJ (US); Bernard Foss, Somerset, NJ (US)

(73) Assignee: TRUTEK CORP., Somerville, NJ (US)

( * ) Notice: Subject to any disclaimer, the term of this patent is extended or adjusted under 35 U.S.C. 154(b) by 0 days.

(21) Appl. No.: 15/390,227

(22) Filed: Dec. 23, 2016

(65) Prior Publication Data
US 2017/0105950 A1   Apr. 20, 2017

(51) Int. Cl.
| | | |
|---|---|---|
| *A61K 31/14* | (2006.01) | |
| *A61K 31/135* | (2006.01) | |
| *A01N 25/24* | (2006.01) | |
| *A61K 9/00* | (2006.01) | |
| *A62B 23/06* | (2006.01) | |

(52) U.S. Cl.
CPC ............ *A61K 31/14* (2013.01); *A61K 9/0014* (2013.01); *A61K 9/0043* (2013.01); *A62B 23/06* (2013.01)

(58) Field of Classification Search
CPC ..... A61K 9/0041; A61K 31/14; A61K 31/135
USPC .......................... 424/407; 514/642, 643, 646
See application file for complete search history.

(56) References Cited

U.S. PATENT DOCUMENTS

| | | |
|---|---|---|
| 1,071,015 A | 8/1913 | Adler |
| 2,237,954 A | 4/1941 | Wilson |
| 2,433,565 A | 12/1947 | Korman |
| 2,751,906 A | 10/1953 | Irvine |
| 2,777,442 A | 4/1955 | Zelano |
| 3,145,711 A | 8/1964 | Berber |
| 3,513,839 A | 5/1970 | Vacante |
| 4,030,491 A | 6/1977 | Mattila |
| 4,052,983 A | 10/1977 | Bovender |
| 4,220,150 A | 9/1980 | King |
| 4,267,831 A | 5/1981 | Aguilar |
| 4,401,117 A | 8/1983 | Gershuny |
| 4,652,282 A | 3/1987 | Ohmori et al. |
| 4,789,504 A | 12/1988 | Ohmori et al. |
| 4,874,659 A | 10/1989 | Ando et al. |
| 5,468,488 A | 11/1995 | Wahi |
| 5,674,481 A | 10/1997 | Wahi |
| 6,494,205 B1 | 12/2002 | Brown |
| 6,844,005 B2 | 1/2005 | Wahi et al. |
| 7,156,098 B2 | 1/2007 | Dolezal et al. |
| 8,163,802 B2 | 4/2012 | Wahi |
| 8,481,480 B1 * | 7/2013 | Lam .................. A61K 8/0208 514/1.1 |
| 2003/0223934 A1 | 12/2003 | Wahi |
| 2004/0261798 A1 | 12/2004 | Rimkus |
| 2009/0235933 A1 | 9/2009 | Wahi |
| 2009/0258946 A1 | 10/2009 | Wahi |
| 2010/0055152 A1 | 3/2010 | Wahi |
| 2010/0278906 A1 * | 11/2010 | Sondgeroth ............ A61K 8/416 424/450 |
| 2014/0143960 A1 * | 5/2014 | Reid ...................... A61K 8/375 8/161 |

\* cited by examiner

*Primary Examiner* — Raymond Henley, III
(74) *Attorney, Agent, or Firm* — Stanley H. Kreman

(57) ABSTRACT

A method of microfiltration of inhaled air for nasal application and product for reducing the risk of inhalation of fine and ultra-fine (i.e., microscopic and submicroscopic) sized atmospheric pollutants by applying a formulation topically to the skin above the upper-lip and in close proximity of the nasal passages. The products of this formulation, when applied, create an electrostatic field for reducing the inhalation of fine and ultra-fine airborne pollutants.

17 Claims, No Drawings

ELECTROSTATICALLY CHARGED NASAL APPLICATION METHOD AND PRODUCT FOR MICRO-FILTRATION

CROSS REFERENCE TO RELATED APPLICATIONS

The following related patents and patent applications have been assigned to TRUTEK Corp., Somerville, N.J. No priority is claimed thereto.
1. U.S. Pat. No. 5,468,488 issued to Wahi on Nov. 21, 1995, based upon application Ser. No. 08/080,775, filed on Jun. 24, 1993.
2. U.S. Pat. No. 5,674,481 issued to Wahi on Oct. 7, 1997, based upon application Ser. No. 08/560,659, filed on Nov. 20, 1995. application Ser. No. 08/560,659 was a continuation-in-part of its parent application Ser. No. 08/080,775.
3. U.S. Pat. No. 6,844,005 issued to Wahi on Jan. 18, 2005 based upon application Ser. No. 10/082,978 filed on Feb. 25, 2002.
4. U.S. Pat. No. 8,163,802 issued to Wahi on Apr. 24, 2012 based upon application Ser. No. 12/467,271 filed on May 16, 2009.
5. U.S. patent application Ser. No. 10/161,821 filed on Jun. 4, 2002 by Wahi, and published as US Patent Application Publication No. 2003/0223934 A1 on Dec. 4, 2003.
6. U.S. patent application Ser. No. 12/475,690 filed on Jun. 1, 2009 by Wahi, and published as US Patent Application Publication No. 2009/0235933 A1 on Sep. 24, 2009.
7. U.S. patent application Ser. No. 12/489,185 filed on Jun. 22, 2009 by Wahi, and published as US Patent Application Publication No. 2009/0258946 A1 on Oct. 15, 2009.
8. U.S. patent application Ser. No. 12/466,382 filed on May 14, 2009 by Wahi, and published as US Patent Application Publication 2010/0055152 A1 on Mar. 4, 2010.

FIELD OF THE INVENTION

The Present Invention relates to the field of protective compositions and microfiltration of various pollutants and particulate matter of fine and ultra-fine (i.e., microscopic and submicroscopic) size range that typically enter the body through the respiratory airway and/or nasal mucosa. More particularly, the Present Invention relates to methods that involve the use of products developed for restricting the flow of (or filtering) the fine and ultra-fine (i.e., microscopic and submicroscopic) ambient airborne pollutants from the nasal passages by creating an electrostatic field in an area around the nose. This reduces or prevents the inhalation of airborne pollutants including but not limited to ultra-fine coal dust, yellow dust, smoke, tobacco smoke and other airborne particulate matter through the nasal passages by filtering the pollutants outside the body before being inhaled.

BACKGROUND OF THE INVENTION

There has been a growing public health concern globally regarding the adverse health effects caused by the inhalation of fine and ultra-fine (submicroscopic/microscopic) particles. From the phenomenon of yellow dust dating back to ancient times to the Great Smog of London in 1952, ambient air contamination is ubiquitous and affects the world's population.

Atmospheric particulate matter or PM, is a mixture of solids and liquid droplets floating in the air. Some particles are released directly from a specific source, while others form in complicated chemical reactions in the atmosphere. $PM_{2.5}$ is particulate matter of 2.5 µm or less in diameter. $PM_{2.5}$ is generally described as fine particles. Ultra-fine particles are those with a diameter less than 0.1 µm or $PM_{0.1}$.

It is generally recognized and well documented that smaller particles have been found to be more harmful long-term to human health. A study by the Bay Area Air Quality Management District entitled "Ultra-fine Particulate Matter Study in the San Francisco Bay Area" (release date 23 Aug. 2010) finds that $PM_{0.1}$ can penetrate pulmonary tissue, enter the bloodstream, and circulate throughout the body, unlike larger particulates. Therefore, $PM_{0.1}$ can damage a number of internal systems that are inaccessible to larger particles. Furthermore, according to the World Health Organization "Health Effects of Particulate Matter", the health effects of inhalable PM are due to exposure over both the short term (hours, days) and long term (months, years) and include respiratory and cardiovascular morbidity, such as aggravation of asthma, respiratory symptoms and an increase in hospital admissions mortality from cardiovascular and respiratory diseases and from lung cancer.

People suffering from asthma and from cardiovascular diseases have been identified to be especially sensitive to air pollution (Palmgren et al., 2003). In epidemiological studies conducted over the past ten years, a very consistent quantitative picture has emerged between the levels of air pollution (especially fine fraction particles) and increases in morbidity and mortality (Palmgren et al., 2003). Furthermore, there is no evidence of a safe level of exposure or a threshold below which no adverse health effects occur.

In addition to ambient air pollution, indoor smoke is also a serious health risk for some 3 billion people who cook and heat their homes with coal and biomass fuels.

The harmful effects related to short-term respiratory exposure to atmospheric particulate matter include:
lung inflammatory reactions,
respiratory symptoms,
adverse effects on the cardiovascular system,
an increase in medication usage,
an increase in hospital admissions, and
an increase in mortality.

However, when one looks at the harmful effects from long-term exposure, a far bleaker picture is seen. These effects include:
an increase in lower respiratory symptoms,
a reduction in lung function in children,
an increase in chronic obstructive pulmonary disease,
a reduction in lung function in adults, and
a reduction in life expectancy, owing mainly to cardio-
  pulmonary mortality and probably to lung cancer.

There is a great need for effective and practical microfiltration of inhaled air in order to reduce inhaled quantities of fine and ultra-fine pollutants and particulate matter such as smoke and dust. Current methods of addressing this widespread problem include face masks which usually cover the nose and mouth, physical nose filters that go outside the nose, or intrusive nose filters that are inserted into the nasal passageway. In general, these methods are inferior to the Present Invention as they are awkward, uncomfortable, cumbersome, and not effective in filtering ultra-fine particulate matter from inhaled air.

SUMMARY OF THE INVENTION

The Present Invention discloses and claims a method to microfilter inhaled air for nasal application and a product for reducing the risk of inhalation of fine and ultra-fine sized atmospheric pollutants wherein a formulation is applied topically to the face above the upper-lip in close proximity of the nasal passages. The products of this formulation, when applied, create an electrostatic field that attracts and captures oppositely charged fine and ultra-fine airborne pollutants, while at the same time, repels similarly charged fine and ultra-fine airborne particles. Therefore, the risk of inhalation is greatly reduced because much fewer oppositely charged and similarly charged particles are inhaled through the nasal passages.

The principal ingredient of the product formulation is Behentrimonium Chloride, which may be obtained as Incroquat Behenyl TMC-85. This ingredient is a naturally derived Behenyl quaternary conditioning agent and self-emulsifier, which was developed for formulations preferred for utilizing a chloride quat.

OBJECT OF THE INVENTION

It is an object of the invention to mitigate the harmful health effects due to the exposure or inhalation of fine and ultra-fine particulate matter contained in airborne pollutants. There are no Drawings.

DISCUSSION OF THE PRIOR ART

To the Applicant's knowledge, the only existing material prior art consists of a patent and published patent applications resulting from the inventions of Ashok Wahi, a co-inventor of the Present Invention. These references are:

| Patent or Publication Number | Issue or Publication Date | Title of Invention |
| --- | --- | --- |
| 5,468,488 | 1995 Nov. 21 | Electrostatically Charged Nasal Application Product and Method |
| 5,674,481 | 1997 Oct. 7 | Electrostatically Charged Nasal Topical Application Product |
| 6,844,005 | 2005 Jan. 18 | Electrostatically Charged Nasal Application Product With Increased Strength |
| 8,163,802 | 2012 Apr. 24 | Electrostatically Charged Multi-Acting Nasal Application Product and Method |
| 2003/0223934 | 2003 Dec. 4 | Electrostatically Charged Nasal Application Diagnostic Product and Method |
| 2009/0235933 | 2009 Sep. 24 | Electrostatically Charged Mask Filter Products And Method For Increased Filtration Efficiency |
| 2009/0258946 | 2009 Oct. 15 | Electrostatically Charged Nasal Application Multi-Purpose Products And Method |
| 2010/0055152 | 2010 Mar. 4 | Antihistamine and Antihistamine-Like Nasal Application, Products and Method |

U.S. Pat. No. 5,468,488 (the '488 patent) is the first patent in a group of two. It is based upon application Ser. No. 08/080,775, filed on 1993 Jun. 24. It is a method patent and not a product patent because it was subject to restriction/election. It teaches and claims a method for restricting the flow of airborne contaminants into a nasal passage by creating an electrostatic field in an area near the nasal passage. The electrostatic field may either repel or attract airborne contaminants. A person applies a topical formulation comprising one or more electrostatic ingredients in a carrier just below the nasal passage. The patent consists of one independent method claim followed by thirteen dependent claims. The independent claim restricts the ingredients to electrostatic polymers having an average cross-sectional area ranging between 1 square millimeter to about 50,000 square millimeters. The resulting electrostatic field can either be positively or negatively charged.

U.S. Pat. No. 5,674,481 (the '481 patent) results from application Ser. No. 08/560,659, filed on 1995 Nov. 20. application Ser. No. 08/560,659 was a continuation-in-part of its parent application Ser. No. 08/080,775. This CIP claims only the product disclosed and claimed in its parent '488 patent. It is applied under the nasal passages as disclosed and claimed in the parent patent. The electrostatic material may be:
1. solid-flexible, semi-rigid or rigid;
2. foam-flexible, semi-rigid or rigid;
3. semi-solid, gel, or hydrogel;
4. solution-ointment, cream, or paste;
a. with or without carrier;
b. with or without substrate; or
c. with or without adhesive.

The patent provides four examples of formulations that may be used to electrostatically attract or repel airborne contaminants and prevent them from entering a person's nasal passages.

The patent consists of one independent product claim followed by ten dependent claims, and application of the claimed product implements the method taught and claimed in the '488 patent.

U.S. Pat. No. 6,844,005 (the '005 patent) results from application Ser. No. 10/082,978 filed on 2002 Feb. 25. There was no parent continuity. The patent is for a product that also uses the method taught in the '488 patent. This patent was allowed after response to an Ex-Parte Quayle action cited in the first office action. In allowing the application, the Examiner reviewed both the '488 and '481 patents. The '005 patent has one independent claim followed by nineteen dependent claims. In allowing the application to issue, what distinguishes the claims of the '005 patent from the earlier two patents is that the claimed formulations (based on claim 1) specified a comprised ingredient as an electrostatic polymer poly(dimethyl diallyl ammonium chloride) in an amount at least 10% by weight. Inclusion of this ingredient in the formulation provides a significantly increased electrostatic charge over the formulations of the '481 patent.

U.S. Pat. No. 8,163,802 (the '802 patent) results from application Ser. No. 12/467,271 filed on 2009 May 16. Priority was based upon two provisional applications filed in 2008. There is no other parent continuity. This patent is both a method and product patent. Claim 1 is an independent method claim, while claim 2 is an independent product claim, which is followed by five claims depending directly or indirectly from claim 1. Claim 8 is an independent product claim, which is followed by fourteen claims depending directly or indirectly from claim 8.

The independent method claim of the '802 patent differs from the independent method claim of the '488 patent in that claim 1 of the '802 patent utilizes a thin film of a formulation in a carrier applied in the vicinity of the nasal passages, wherein the formulation includes ingredients that electrostatically attract airborne particulates, causing the particulates to adhere to the thin film, and inactivating the particulates, thereby rendering them harmless. Claims 2 and 8 recite formulations not claimed in either the '408 or '005 patents. The Examiner reviewed and considered the '488, '481, and '005 patents as well as the Applicant's Application Publication 2003/0223934. All 23 claims were allowed.

The published US patent applications listed in the above table did not mature into patents. US Patent Application Publication No. 2003/0223934 A1 teaches a diagnostic method that uses the methodology of the '488 patent. The formulation is applied to a patient in the vicinity of the nasal passage and then removed and analyzed for the presence of particulates.

US Patent Application Publication No. 2009/0235933 A1 teaches the use of an electrostatically charged surgical or permeable mask that prevents contaminants from entering the nose or mouth of the person wearing the mask. The mask provided increased filtration efficiency of commercially available masks. Here, the mask repels some particulates and attracts and traps other particulates.

US Patent Application Publication No. 2009/0258946 A1 teaches a product formulation that includes a cationic agent, which is:
Polyquaternium-6,
Polyquaternium-7,
Polyquaternium-10,
Polyquaternium-22,
Polyquaternium-88,
Cocodimonium Hydroxypropyl Hydrolyzed Keratin,
Hydroxypropyl Trimonium Hydrolyzed Soy Protein,
Hydroxypropyl Trimonium Silk Protein,
Hydroxypropyl Trimonium Wheat Protein, or
Hydroxypropyl Trimonium Oat Protein.

Another product formulation would be a nasal spray including an ingredient which is one of those listed above.

US Patent Application Publication No. 2010/0055152 A1 teaches a method and product applied to the vicinity of a person's nasal passages, creating a barrier that prevents airborne allergens from contact with nasal passages. The application contains some previously undisclosed formulations.

DETAILED DESCRIPTION OF THE INVENTION

Studies have long shown that there is a strong link between exposure to airborne contaminants and adverse health effects. Despite minor improvements of air quality over the years, the health risks associated with ambient air pollution remain a public health concern. There is sufficient evidence that reducing the inhalation of airborne pollutants can reduce the burden of disease from stroke, heart disease, lung cancer, and both chronic and acute respiratory diseases such as asthma and adverse pregnancy outcomes.

The Present Invention aims to reduce the inhalation of fine and ultra-fine airborne pollutants and, therefore, alleviate the adverse health effects they cause by creating an electrostatic field around the nasal passages for microfiltration which cannot be expected by current methods of filtration.

Particulates having diameters larger than about 80-100 microns are visible to the naked eye. Grains of beach sand are slightly larger than 100 microns in diameter. Although some pollen particles are visible to the naked eye, most are not. Fine particulates are those not visible to the naked eye. Their diameters range from 0.1 micron to about 80 microns. Fine particle classification includes pollen, dust, bacteria, mulled flour, coal dust, and asbestos. Ultra-fine particulates have a diameter of less than 0.1 micron. These include tobacco smoke, viruses, and colloidal silica.

The topical products of the formulations of the Present Invention contain quaternary compounds that are cationic in nature, which attract oppositely-charged particles, and which repel similarly-charged particles. Therefore, these products, when applied to the skin, reduce or prevent the inhalation/flow of airborne pollutants including but not limited to ultra-fine coal dust, yellow dust, smoke, smoke including tobacco and industrial and other airborne particulate matter to the nasal passages by filtering the pollutants outside the body before being inhaled.

In order to accomplish the above objects of the invention, an aqueous formulation is developed.

A formulation of the invention comprises:
water,
at least one quaternary compound,
a preservative,
a conditioner,
an emulsifier, It may further comprise without limitation a combination of the following:
a surfactant,
a thickener,
an emollient,
a humectant, and
a binder.

The principal ingredient of all of the formulations herein is Behentrimonium Chloride. It is a long-chain polymer having the following chemical structure:

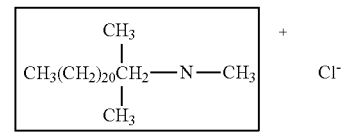

Another name for the polymer is docosyltrimethylammonium chloride. It is normally used as an antistatic agent and, sometimes, a disinfectant. It is commonly found in conditioners, hair dye, and mousse, and also in detergents. In water treatment, it acts as an algaecide. it is a naturally derived Behenyl quaternary conditioning agent and self-emulsifier, which was developed for formulations preferred for utilizing a chloride quat.

Behentrimonium Chloride is just one example of a class of compounds that may be used in the formulation. As a substitute ingredient, one may use a chloride based quaternary long-chain polymer. A long-chain polymer is defined as having at least 22 links. Quaternary compounds in the previous patents and applications discussed previously had shorter chains ranging between 10-18 links, and were keratin protein-based quaternary compounds.

It has been experimentally verified that formulations containing Behentrimonium Chloride, when applied in the vicinity of nasal passages, prevent fine and ultra-fine particles from entering the nasal passages by creating an electrostatic field that trap these particles prior to inhalation. This result was unanticipated and unexpected in the prior patents and patent applications listed above, which only prevent inhalation of much larger particulates.

Examples of typical formulations found to be effective appear in the eight tables that follow. Percentages are given by weight.

TABLE 1

| Ingredient | Percent Range | Function |
| --- | --- | --- |
| Water | 70%-90% | Solvent, Moisturizer |
| Behentrimonium Chloride | 8%-12% | Conditioner, Quaternary, Emulsifier |

TABLE 1-continued

| Ingredient | Percent Range | Function |
|---|---|---|
| Hydroxyethyl Cellulose, Sodium Acetate, Cellulose | 0.5%-2% | Thickener |
| Quaternary Ammonium Compounds, Benzyl-C12-16-alkyldimethyl, Chlorides, Ethanol | 0.25%-1% | Cationic, Quaternary, Biocide |
| Glycerin | 0.5%-3% | Humectant |

TABLE 2

| Ingredient | Percent Range | Function |
|---|---|---|
| Behentrimonium Chloride | 8%-12% | Conditioner, Quaternary, Emulsifier |
| Glycerin | 8%-12% | Humectant |
| Water | 50%-70% | Solvent, Moisturizer |
| Hydroxyethyl Cellulose, Sodium Acetate, Cellulose | 0.5%-2% | Thickener |
| Quaternary Ammonium Compounds, Benzyl-C12-16-alkyldimethyl, Chlorides, Ethanol | 0.1%-0.5% | Cationic, Quaternary, Biocide |
| Phenoxyethanol, Methylparaben, Ethylparaben, Propylparaben, Butylparaben, Isobutylparaben | 0.5%-2% | Preservative |
| Lysine HCL | 0.5%-2% | Conditioner, Biocide |
| Caprylic, Capric Triglyceride | 4%-6% | Emollient, Lubricant Solvent |
| Dimethicone | 1%-3% | Conditioning Emollient |
| Glyceryl Stearate, PEG-100 Stearate | 2%-4% | Emulsifier |

TABLE 3

| Ingredient | Percent Range | Function |
|---|---|---|
| Behentrimonium Chloride | 8%-12% | Conditioner, Quaternary, Emulsifier |
| Glycerin | 8%-12% | Humectant |
| Water | 50%-70% | Solvent, Moisturizer |
| Hydroxyethyl Cellulose, Sodium Acetate, Cellulose | 0.5%-2% | Thickener |
| Quaternary Ammonium Compounds, Benzyl-C12-16-alkyldimethyl, Chlorides, Ethanol | 0.1%-0.5% | Cationic, Quaternary, Biocide |
| Phenoxyethanol, Methylparaben, Ethylparaben, Propylparaben, Butylparaben, Isobutylparaben | 0.5%-2% | Preservative |
| Lysine HCL | 0.5%-2% | Conditioner, Biocide |
| Caprylic, Capric Triglyceride | 4%-6% | Emollient, Lubricant Solvent |
| Dimethicone | 1%-3% | Conditioning Emollient |
| Steareth-2 | 0.5%-2% | Emulsifier, Moisturizer |
| Steareth-21 | 0.5%-2% | Emulsifier, Moisturizer |
| Menthol | 0.4%-0.6% | Coating Agent/Fragrance |

TABLE 4

| Ingredient | Percent Range | Function |
|---|---|---|
| Behentrimonium Chloride | 8%-12% | Conditioner, Quaternary, Emulsifier |
| Glycerin | 8%-12% | Humectant |
| Water | 50%-70% | Solvent, Moisturizer |
| Hydroxyethyl Cellulose, Sodium Acetate, Cellulose | 0.5%-2% | Thickener |
| Quaternary Ammonium Compounds, Benzyl-C12-16-alkyldimethyl, Chlorides, Ethanol | 0.1%-0.5% | Cationic, Quaternary, Biocide |
| Phenoxyethanol, Methylparaben, Ethylparaben, Propylparaben, Butylparaben, Isobutylparaben | 0.5%-1.5% | Preservative |
| Lysine HCL | 0.5%-1.5% | Conditioner, Biocide |
| Caprylic, Capric Triglyceride | 4%-6% | Emollient, Lubricant Solvent |
| Dimethicone | 1%-3% | Conditioning Emollient |
| Steareth-2 | 2%-4% | Emulsifier, Moisturizer |
| Steareth-21 | 2%-4% | Emulsifier, Moisturizer |
| Menthol | 0.4%-0.6% | Cooling Agent/Fragrance |

TABLE 5

| Ingredient | Percent Range | Function |
| --- | --- | --- |
| Behentrimonium Chloride | 8%-12% | Conditioner, Quaternary, Emulsifier |
| Glycerin | 8%-12% | Humectant |
| Water | 50%-70% | Solvent, Moisturizer |
| Hydroxyethyl Cellulose, Sodium Acetate, Cellulose | 2%-4% | Thickener |
| Quaternary Ammonium Compounds, Benzyl-C12-16-alkyldimethyl, Chlorides, Ethanol | 0.1%-0.4% | Cationic, Quaternary, Biocide |
| Phenoxyethanol, Methylparaben, Ethylparaben, Propylparaben, Butylparaben, Isobutylparaben | 0.5%-1.5% | Preservative |
| Lysine HCL | 0.2%-0.7% | Conditioner, Biocide |
| Caprylic, Capric Triglyceride | 4%-6% | Emollient, Lubricant Solvent |
| Dimethicone | 1%-3% | Conditioning Emollient |
| Steareth-2 | 2%-4% | Emulsifier, Moisturizer |
| Steareth-21 | 2%-4% | Emulsifier, Moisturizer |
| Menthol | 0.4%-0.6% | Cooling Agent/ Fragrance |

TABLE 6

| Ingredient | Percent Range | Function |
| --- | --- | --- |
| Behentrimonium Chloride | 8%-12% | Conditioner, Quaternary, Emulsifier |
| Glycerin | 8%-12% | Humectant |
| Water | 50%-70% | Solvent, Moisturizer |
| Hydroxyethyl Cellulose, Sodium Acetate, Cellulose | 2%-4% | Thickener |
| Quaternary Ammonium Compounds, Benzyl-C12-16-alkyldimethyl, Chlorides, Ethanol | 0.1%-0.4% | Cationic, Quaternary, Biocide |
| Phenoxyethanol, Methylparaben, Ethylparaben, Propylparaben, Butylparaben, Isobutylparaben | 0.5%-1.5% | Preservative |
| Lysine HCL | 0.2%-0.7% | Conditioner, Biocide |
| Caprylic, Capric Triglyceride | 4%-6% | Emollient, Lubricant Solvent |
| Dimethicone | 1%-3% | Conditioning Emollient |
| Steareth-2 | 3%-4% | Emulsifier, Moisturizer |
| Steareth-21 | 3%-4% | Emulsifier, Moisturizer |
| Menthol | 0.4%-0.6% | Cooling Agent/ Fragrance |

TABLE 7

| Ingredient | Percent Range | Function |
| --- | --- | --- |
| Behentrimonium Chloride | 8%-12% | Conditioner, Quaternary, Emulsifier |
| Glycerin | 8%-12% | Humectant |
| Water | 50%-70% | Solvent, Moisturizer |
| Hydroxyethyl Cellulose, Sodium Acetate, Cellulose | 2%-4% | Thickener |
| Quaternary Ammonium Compounds, Benzyl-C12-16-alkyldimethyl, Chlorides, Ethanol | 0.1%-0.4% | Cationic, Quaternary, Biocide |
| 2-Phenoxyethanol | 0.7%-1.2% | Preservative |
| Potassium Sorbate | 0.1%-0.4% | Preservative |
| Caprylic, Capric Triglyceride | 4%-6% | Emollient, Lubricant Solvent |
| Dimethicone | 1%-3% | Conditioning Emollient |
| Steareth-2 | 3%-4% | Emulsifier, Moisturizer |
| Steareth-21 | 2%-3% | Emulsifier, Moisturizer |
| Menthol | 0.4%-0.9% | Cooling Agent/ Fragrance |

TABLE 8

| Ingredient | Percent Range | Function |
| --- | --- | --- |
| Behentrimonium Chloride | 8%-12% | Conditioner, Quaternary, Emulsifier |
| Glycerin | 8%-12% | Humectant |
| Water | 50%-70% | Solvent, Moisturizer |
| Hydroxyethyl Cellulose, Sodium Acetate, Cellulose | 2%-4% | Thickener |

TABLE 8-continued

| Ingredient | Percent Range | Function |
|---|---|---|
| Quaternary Ammonium Compounds, Benzyl-C12-16-alkyldimethyl, Chlorides, Ethanol | 0.1%-0.4% | Cationic, Quaternary, Biocide |
| Phenoxyethanol, Methylparaben, Ethylparaben, Propylparaben, Butylparaben, Isobutylparaben | 0.5%-1.5% | Preservative |
| Lysine HCL | 0.5%-1.5% | Conditioner, Biocide |
| Caprylic, Capric Triglyceride | 4%-6% | Emollient, Lubricant Solvent |
| Dimethicone | 1%-3% | Conditioning Emollient |
| Steareth-2 | 3%-4% | Emulsifier, Moisturizer |
| Steareth-21 | 2%-3% | Emulsifier, Moisturizer |
| Menthol | 0.4%-0.9% | Cooling Agent/Fragrance |

All of the formulations described in TABLES 1 to 8 representing various embodiments of the Present Invention operate in the manner that was disclosed herein. The same results may be achieved by varying the percentages for the key ingredients. Varying the percentages for the ingredients affects the efficacy and consistency of the formulation.

Another ingredient that may be included in the formulation is Cocodimonium Hydroxypropyl Hydrolyzed Keratin. This is a quaternized permanent conditioning protein developed specifically to give immediate and perceptible conditioning effects in salon hair care products. It offers both permanent conditioning and enhanced substantivity. It consists of a cystine-containing keratin protein (average molecular weight 1000) and a fatty moiety ($C_{10}$-$C_{18}$) attached to the protein backbone.

Ideally, the formulations are applied as a thin film around the vicinity of the nasal passages to prevent inhalation through the nose. However, it may be applied along a person's entire face for greater effectiveness. The adhesion of the thin film should be adjusted to permit the film to stick to the skin or tissue and the cohesion of the formulation should be adjusted to provide adequate impermeability to the thin film.

The formulation may be contained in a liquid further comprising a solvent that evaporates quickly. Alternatively, it may be contained in an ointment, a gel, or a cream.

The desired results may be achieved by varying the ingredients and their composition by those skilled in the art without undue experimentation.

GLOSSARY

Regarding the disclosure and claims in this Present patent application, the co-inventors choose to be their own lexicographers. The definitions of terms contained within the specification, abstract, and claims of this Application supersede the plain and ordinary meaning of those terms.

1. Fine Particulate Matter or Fine Particle—particles not visible to the naked eye, having diameters less than or equal to 80 microns and greater than 0.1 micron.
2. Ultra-Fine Particulate Matter or Ultra-Fine Particle—particles having diameters less than or equal to 0.1 micron.
3. Microscopic—less than or equal to 80 microns and greater than 0.1 micron in size.
4. Sub-Microscopic—less than or equal to 0.1 µm in size.
5. Long-Chain Polymer—a polymer with at least 22 links.

We claim:

1. A formulation for electrostatically inhibiting inhalation of fine and ultra-fine particulate matter by a person, wherein said inhibiting occurs upon application of said formulation to the person's face between the upper lip and nasal passages, said formulation containing ingredients comprising:
   a) a chloride based quaternary long chain-polymer that creates an electrostatic field;
   b) a thickening agent; and
   c) a plasticizing agent,
   wherein after application of said formulation to the person's face between the upper lip and nasal passages,
   i) the formulation forms a stationary film that adheres to the person's face where applied;
   ii) the electrostatic field has sufficient strength to repel similarly charged fine and ultra-fine particulate matter;
   iii) the electrostatic field has sufficient strength to attract oppositely charged fine and ultra-fine particulate matter,
   such that said oppositely charged fine and ultra-fine particulate matter adheres to the stationary film.

2. The formulation of claim 1 wherein the chloride based quaternary long-chain polymer is Behentrimonium Chloride.

3. The formulation of claim 1 wherein the thickening agent is Hydroxyethyl Cellulose.

4. The formulation of claim 1 wherein the plasticizing agent is Caprylic/Capric Triglyceride.

5. The formulation of claim 1 comprising Behentrimonium Chloride, Hydroxymethyl Cellulose, and Caprylic/Capric Triglyceride.

6. The formulation of claim 1 further comprising water.

7. The formulation of claim 1, wherein the formulation is contained in an ointment.

8. The formulation of claim 1, wherein the formulation is contained in a gel.

9. The formulation of claim 1, wherein the formulation is contained in a cream.

10. A formulation for electrostatically inhibiting inhalation of fine and ultra-fine particulate matter by a person, wherein said inhibiting occurs upon application of said formulation to the person's face between the upper lip and nasal passages, said formulation containing ingredients consisting essentially of:
    a) a chloride based quaternary long chain-polymer that creates an electrostatic field;
    b) a thickening agent;
    c) a plasticizing agent; and
    d) water,
    wherein after application of said formulation to the person's face between the upper lip and nasal passages,
    i) the formulation forms a stationary film that adheres to the person's face where applied;
    ii) the electrostatic field has sufficient strength to repel similarly charged fine and ultra-fine particulate matter;
    iii) the electrostatic field has sufficient strength to attract oppositely charged fine and ultra-fine particulate matter,
    such that said oppositely charged fine and ultra-fine particulate matter adheres to the stationary film.

11. The formulation of claim 10 wherein the chloride based quaternary long-chain polymer is Behentrimonium Chloride.

12. The formulation of claim 10 wherein the thickening agent is Hydroxyethyl Cellulose.

13. The formulation of claim 10 wherein the plasticizing agent is Caprylic/Capric Triglyceride.

14. The formulation of claim 10 wherein the chloride based quaternary long-chain polymer is Behentrimonium Chloride; and the thickening agent is Hydroxyethyl Cellulose; and the plasticizing agent is Caprylic/Capric Triglyceride.

15. The formulation of claim 10, wherein the formulation is contained in an ointment.

16. The formulation of claim 10, wherein the formulation is contained in a gel.

17. The formulation of claim 10, wherein the formulation is contained in a cream.

* * * * *